US012582494B2

(12) United States Patent
Oguri

(10) Patent No.: US 12,582,494 B2
(45) Date of Patent: Mar. 24, 2026

(54) MANIPULATOR FOR MICROSCOPIC WORK

(71) Applicant: F.MED CO., LTD., Fukuoka (JP)

(72) Inventor: Susumu Oguri, Fukuoka (JP)

(73) Assignee: F.MED CO., LTD., Fukuoka (JP)

( * ) Notice: Subject to any disclaimer, the term of this patent is extended or adjusted under 35 U.S.C. 154(b) by 450 days.

(21) Appl. No.: 18/018,744

(22) PCT Filed: Jul. 30, 2020

(86) PCT No.: PCT/JP2020/029243
§ 371 (c)(1),
(2) Date: Jan. 30, 2023

(87) PCT Pub. No.: WO2022/024296
PCT Pub. Date: Feb. 3, 2022

(65) Prior Publication Data
US 2023/0355340 A1       Nov. 9, 2023

(51) Int. Cl.
*A61B 34/00* (2016.01)
*A61B 34/30* (2016.01)
(52) U.S. Cl.
CPC .............. *A61B 34/72* (2016.02); *A61B 34/30* (2016.02)
(58) Field of Classification Search
CPC ...... A61B 34/30; A61B 34/72; B25J 17/0266; B25J 7/00; B25J 9/0042; B25J 9/146; G02B 21/32
See application file for complete search history.

(56) References Cited

U.S. PATENT DOCUMENTS

2010/0010504 A1    1/2010  Simaan et al.
2011/0277775 A1*   11/2011  Holop ................... A61B 34/35
                                                                128/849
2012/0095596 A1    4/2012  Cole et al.
(Continued)

FOREIGN PATENT DOCUMENTS

EP         2 907 467 A1      8/2015
EP         3 372 350 A1      9/2018
(Continued)

OTHER PUBLICATIONS

Apr. 2, 2024 Extended Search Report issued European Patent Application No. 20947001.2.
(Continued)

*Primary Examiner* — Mohamed G Gabr
*Assistant Examiner* — Khoa Tan Le
(74) *Attorney, Agent, or Firm* — Oliff PLC

(57) ABSTRACT
A parallel link mechanism is configured so that a plurality of linear actuators which are supported on a base are used to linearly shift one end part of each of links so as to move an end effector coupled to the other end parts of the links. The manipulator further includes a rotation support part that is provided between the end effector and the parallel link mechanism and that supports the end effector rotatably around a predetermined rotational axis, and a hydraulic drive mechanism that generates in the end effector rotating power around the rotational axis. The manipulator imparts, from the exterior to the hydraulic drive mechanism, change in the working-fluid hydraulic pressure so as to generate movement for rotating the end effector.

4 Claims, 17 Drawing Sheets

(56) References Cited

U.S. PATENT DOCUMENTS

| | | |
|---|---|---|
| 2015/0230869 A1 | 8/2015 | Shim et al. |
| 2018/0238883 A1 | 8/2018 | Penny et al. |
| 2019/0160650 A1* | 5/2019 | Oguri .................... A61B 34/30 |
| 2020/0030969 A1 | 1/2020 | Iwazaki |

FOREIGN PATENT DOCUMENTS

| | | |
|---|---|---|
| JP | S58-163805 A | 9/1983 |
| JP | H07-12232 A | 1/1995 |
| JP | H09-225868 A | 9/1997 |
| JP | 2010-504151 A | 2/2010 |
| JP | 2015-150425 A | 8/2015 |
| JP | 2017-087322 A | 5/2017 |
| WO | 2017/078022 A1 | 5/2017 |

OTHER PUBLICATIONS

Aug. 6, 2024 Office Action issued in Japanese Patent Application No. 2022-189006.
Oct. 13, 2020 Search Report issued in International Patent Application No. PCT/JP2020/029243.
Jan. 30, 2024 Office Action issued in Japanese Patent Application No. 2022-189006.
Jan. 31, 2023 Interntional Preliminary Report on Patentability issued in International Patent Application No. PCT/JP2020/029243.
Feb. 2, 2026 Extended European Search Report issued in European Application No. 25209525.2.

* cited by examiner

19e

19g

17g

17e(17f)

MANIPULATOR FOR MICROSCOPIC WORK

TECHNICAL FIELD

The present invention relates to a manipulator for microscopic work.

BACKGROUND ART

In so-called microsurgery in which surgery is performed on a microscopic surgery object under a microscope such as inosculation of thin blood vessels each having a diameter of about 0.5 mm to about 2 mm, nerves, or lymphatic vessels in surgery related to orthopedic surgery or plastic surgery or reconstructive surgery of a defect, the surgery object is minute, and hence extremely accurate and precise work is required and the surgery requires skill. In addition, the surgery tends to require a long time period due to its difficulty and, in the case of such surgery that requires the long time period, a burden on a surgeon is increased. For this reason, the number of surgeons capable of performing the microsurgery has been limited compared with its necessity, and it has been impossible to perform the microsurgery frequently.

Herein, when utilization of a manipulator (robot) that has been significantly advanced recently in terms of technology is examined, a master-slave manipulator is capable of reproducing human motions and also performing operations of scaled-down human motions and, if operations related to surgery are performed by the manipulator that operates accurately, it is possible to reduce the burden on the surgeon while eliminating the influence of shaky hands or the like to secure accuracy, and efficiency of the surgery is expected to be improved.

To cope with this, the present inventors have proposed a microscopic work assistance system capable of performing work assistance efficiently by properly performing operations related to work by remote control and reducing a burden on an operator, and a manipulator for microscopic work that is used in the microscopic work assistance system (see PTL 1).

CITATION LIST

Patent Literature

PTL 1

Japanese Patent Application Publication No. H2017-87322

SUMMARY OF INVENTION

Technical Problem

In the manipulator for microscopic work disclosed in PTL 1, forceps provided at a tip have been operated by a parallel link mechanism. Herein, an operation of twisting (rotating) the forceps not only in microsurgery but also in surgical operations is important as work performed on a surgery object by a surgeon and, in the manipulator for microscopic work disclosed in PTL 1, the operation thereof has been implemented by operating the parallel link mechanism.

However, when the operation of twisting the forceps is implemented by operating the parallel link mechanism, in some cases, it has not been possible to reliably perform control for rotating the forceps only by a minute angle smoothly.

The present invention has been made in view of the above problem, and an object thereof is to provide a manipulator for microscopic work capable of controlling the rotational operation of an end effector smoothly and reliably.

Solution to Problem

In order to solve the above problem, a manipulator for microscopic work according to one aspect of the present invention is a manipulator for microscopic work that executes a predetermined operation related to microscopic work on a work object instead of a person. The manipulator for microscopic work includes: a parallel link mechanism with three or more degrees of freedom, the parallel link mechanism includes: abase that is supported on a predetermined part in a space in which the work object is present; an end effector that is configured to handle the work object or an instrument for work; and a plurality of links that are disposed in parallel between the base and the end effector, the parallel link mechanism configured to be capable of changing a position and an orientation of the end effector with respect to the base in a predetermined range. The parallel link mechanism configured so that a plurality of linear actuators supported on the base are used to linearly shift one end part of each of the plurality of links so as to move the end effector coupled to another end part of each link. The parallel link mechanism further includes a rotation support part that is provided between the end effector and the parallel link mechanism and is configured to support the end effector rotatably around a predetermined rotational axis and a hydraulic drive mechanism that is configured to generate rotating power around the rotational axis to the end effector. The parallel link mechanism is configured to impart, from the exterior to the hydraulic drive mechanism, change in working-fluid hydraulic pressure so as to generate movement for rotating the end effector.

Advantageous Effects of Invention

According to the present invention, it is possible to implement the manipulator for microscopic work capable of controlling the rotational operation of the end effector smoothly and reliably.

DESCRIPTION OF EMBODIMENTS

Figure 1:
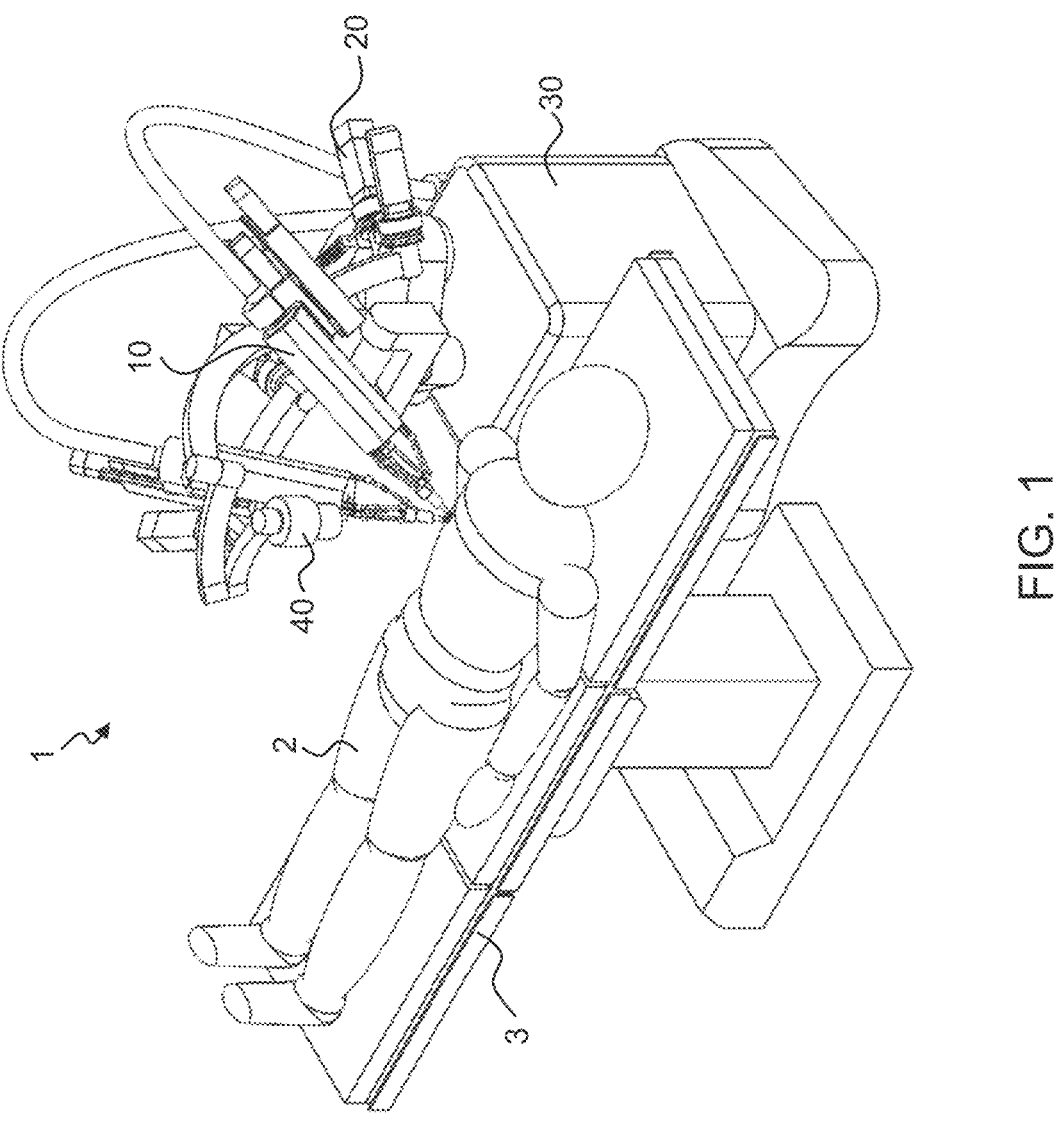
FIG. 1 is a perspective view showing a schematic configuration of a device for microscope work to which a manipulator for microscopic work according to an embodiment is applied.

Hereinbelow, an embodiment of the present invention will be described with reference to the drawings. Note that the embodiment described below is not intended to limit the invention according to the scope of claims, and all elements and their combinations described in the embodiment are not necessarily essential for the solution of the invention.

Note that, in the drawings for describing the embodiment, parts having the same functions are designated by the same reference symbols, and the repeated description thereof will be omitted.

In the present embodiment, a description will be given of a device for microscopic work to which a manipulator for microscopic work for assisting surgery corresponding to microsurgery serving as microscopic work is applied.

Figure 2:
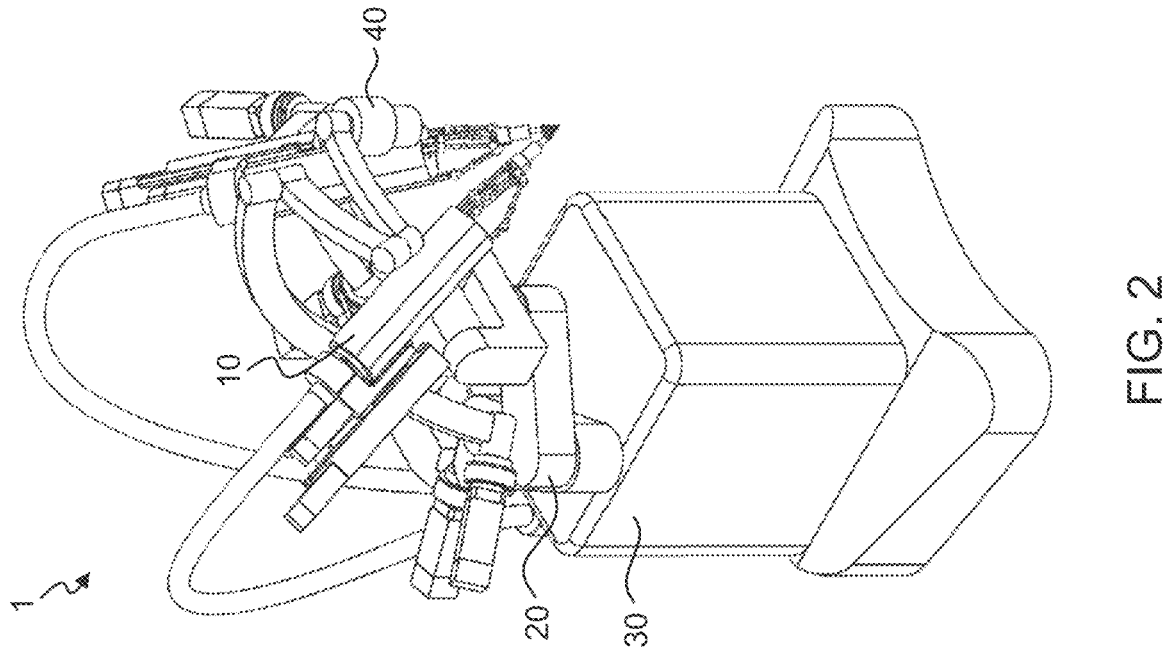
FIG. 2 is a perspective view showing the schematic configuration of the device for microscopic work to which the manipulator for microscopic work according to the embodiment is applied.
Figure 3:
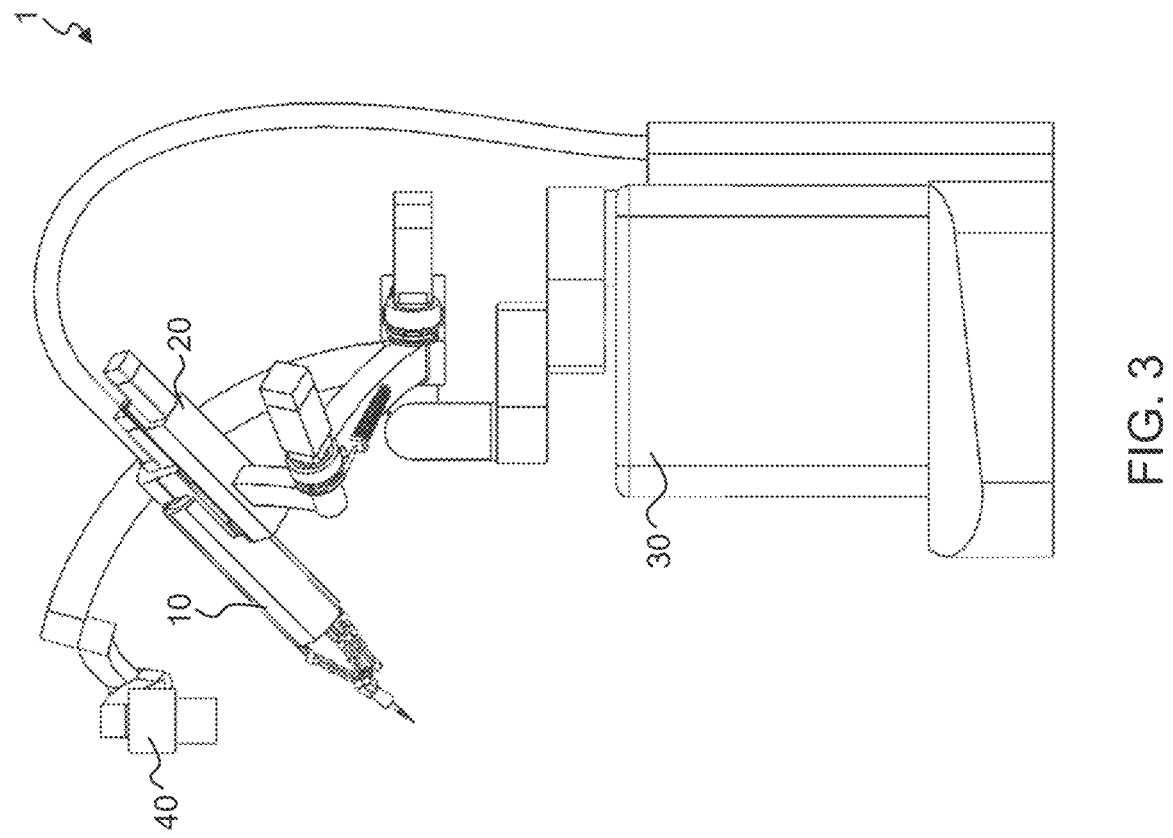
FIG. 3 is a side view showing the schematic configuration of the device for microscopic work to which the manipulator for microscopic work according to the embodiment is applied.

As shown in FIGS. 1 to 3, a device for microscopic work 1 according to the present embodiment includes a manipulator for microscopic work 10 according to the present embodiment, a robot part 20 in which the manipulator for microscopic work 10 is mounted to a tip part, a base 30 that supports the robot part 20 from below, an imaging part 40 that is mounted to the base 30 similarly and captures an image of a surgery object, and a control part that is not shown and controls operations of the entire device for microscopic work 1. In addition, a display part is provided on an as needed basis.

The robot part 20 has three degrees of freedom of rotation and one degree of freedom of translation in a radial direction. In examples shown in the drawings, a pair of the robot part 20 and the manipulator for microscopic work 10 are provided on the base 30, but the number of robot parts 20 and the number of manipulators for microscopic work 10 are not particularly limited.

The imaging part 40 captures images of a tip operation part of an end effector of the manipulator for microscopic work 10 described later, and a surgery object, and is disposed at a position above, e.g., the robot part 20 that allows the imaging part 40 to overlook at least a tip of the manipulator for microscopic work 10 and the surgery object. This imaging part 40 is a known video camera capable of acquiring a captured image having high resolution that can secure reproducibility even when the captured image is enlarged with the same magnification as that of a conventional microscope for microsurgery and, therefore, the detailed description thereof will be omitted.

The display part displays the image of the surgery object acquired by the imaging part 40 to a user such that the user can visually recognize the surgery object while enlarging the image of the surgery object on an as needed basis. This display part is a known display device such as a liquid crystal display capable of displaying the image obtained by imaging with high resolution and, therefore, the detailed description thereof will be omitted.

The base 30 includes a movement mechanism that is not shown, and is configured to be movable to a predetermined position based on movement support from the control part on a floor of an operating room that is not shown together with the manipulator for microscopic work 10, the robot part 20, and the imaging part 40 provided on the base 30. With this, the device for microscopic work 1 of the present embodiment is allowed to move close to or away from a surgical table 3 on which a patient 2 serving as the surgery object shown in FIG. 1 lies and, further, it is possible to dispose at least the tip part of the manipulator for microscopic work 10 at a surgery part of the patient 2.

Figure 4:
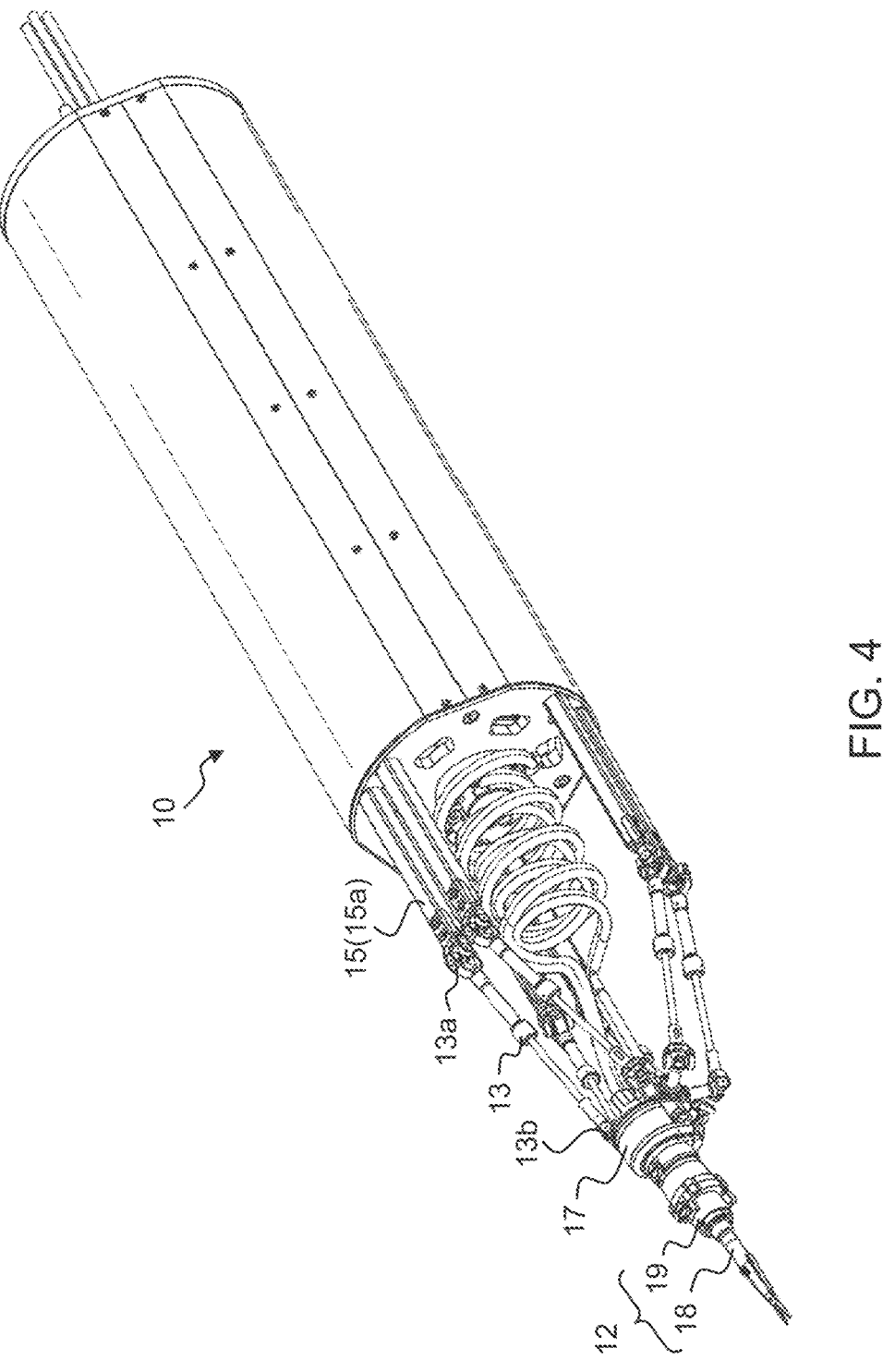
FIG. 4 is a perspective view showing the manipulator for microscopic work according to Embodiment.
Figure 5:
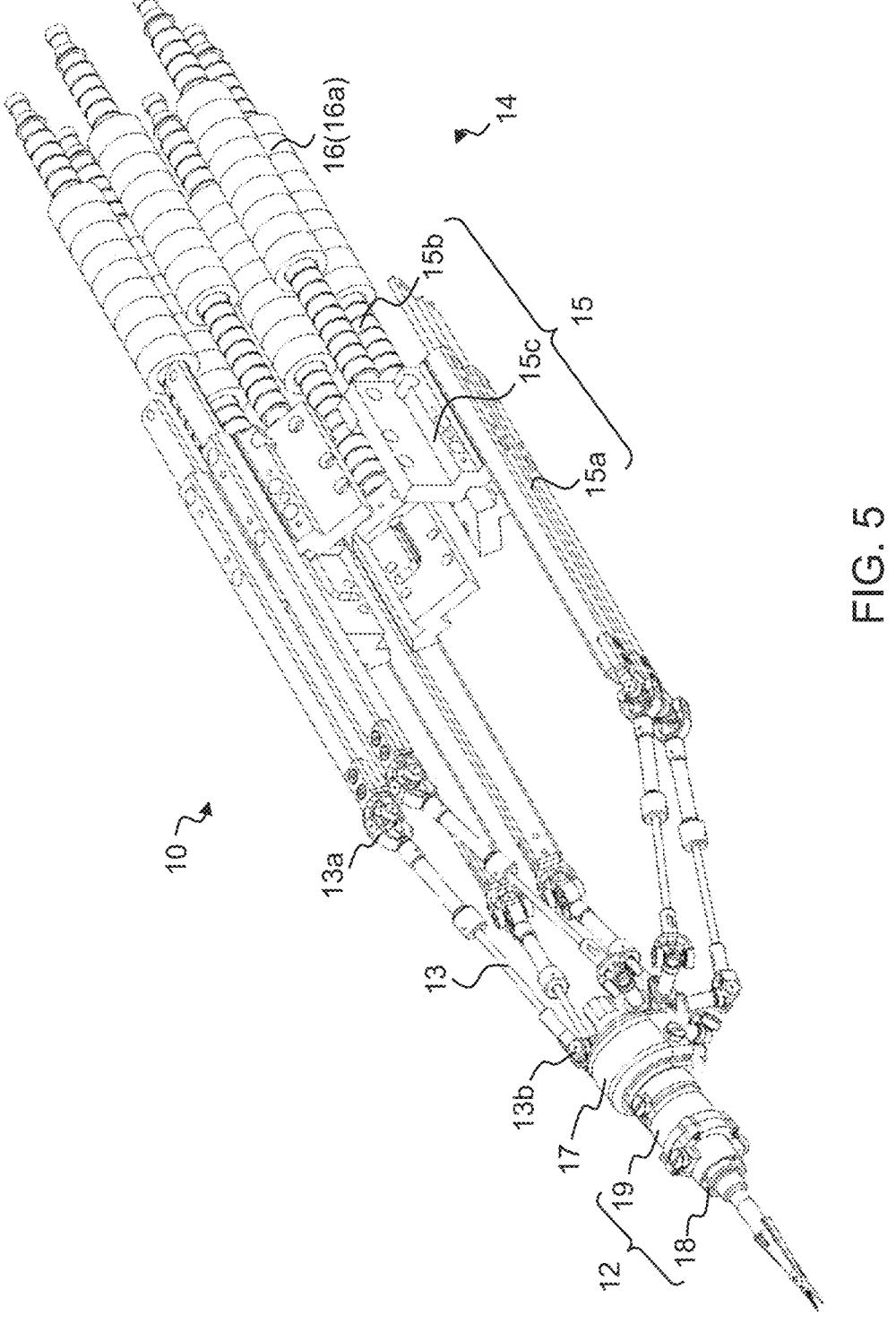
FIG. 5 is a perspective view showing a principal part of the manipulator for microscopic work according to the embodiment.
Figure 6:
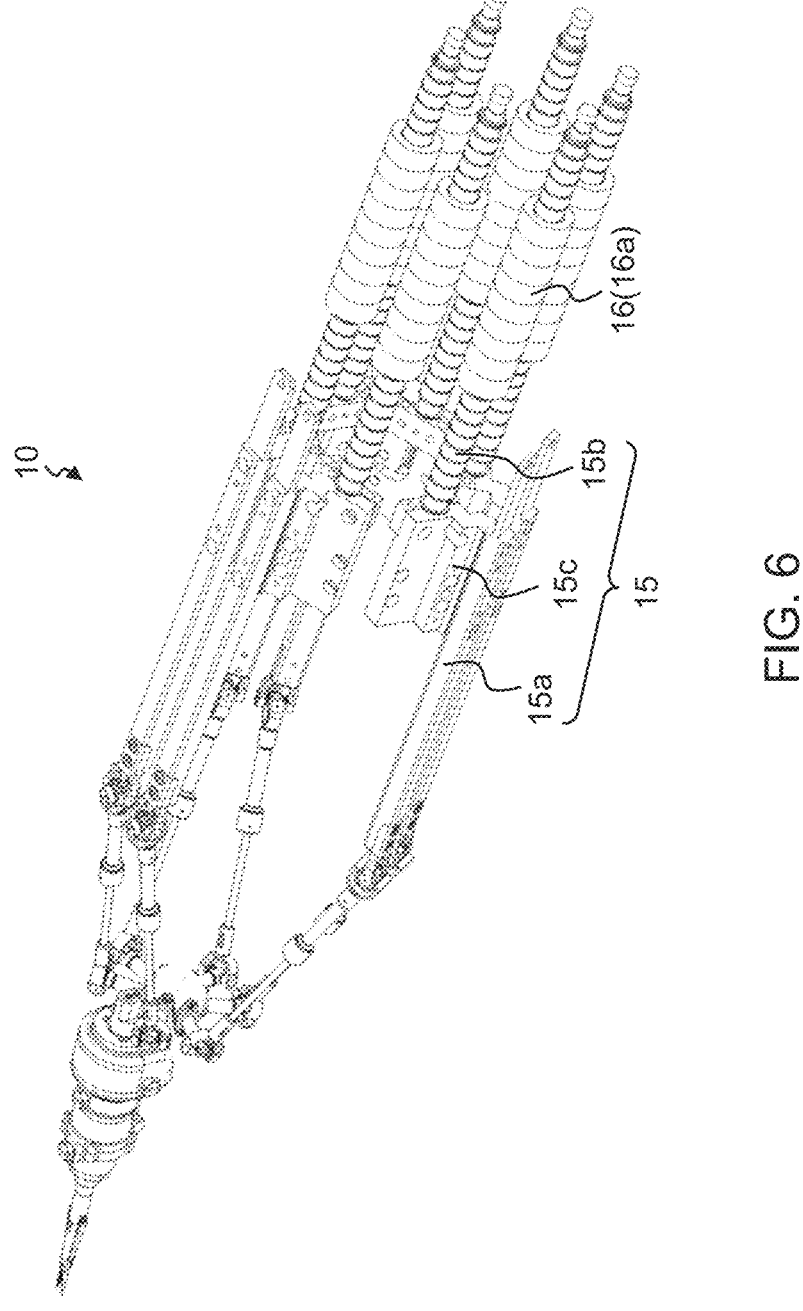
FIG. 6 is a perspective view showing the principal part of the manipulator for microscopic work according to the embodiment.
Figure 7:
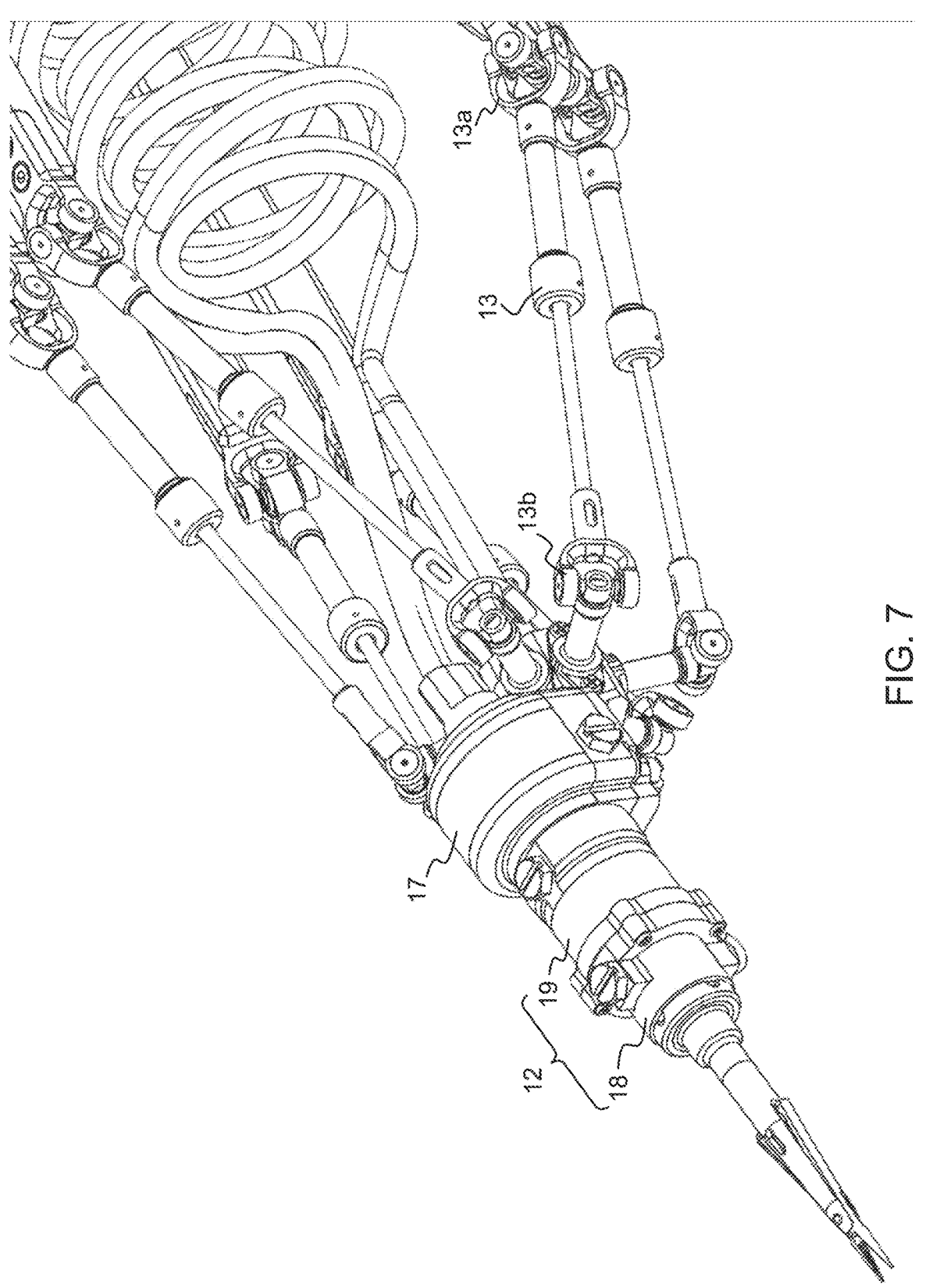
FIG. 7 is a perspective view showing an end effector and a rotation support part of the manipulator for microscopic work according to the embodiment.
Figure 8:
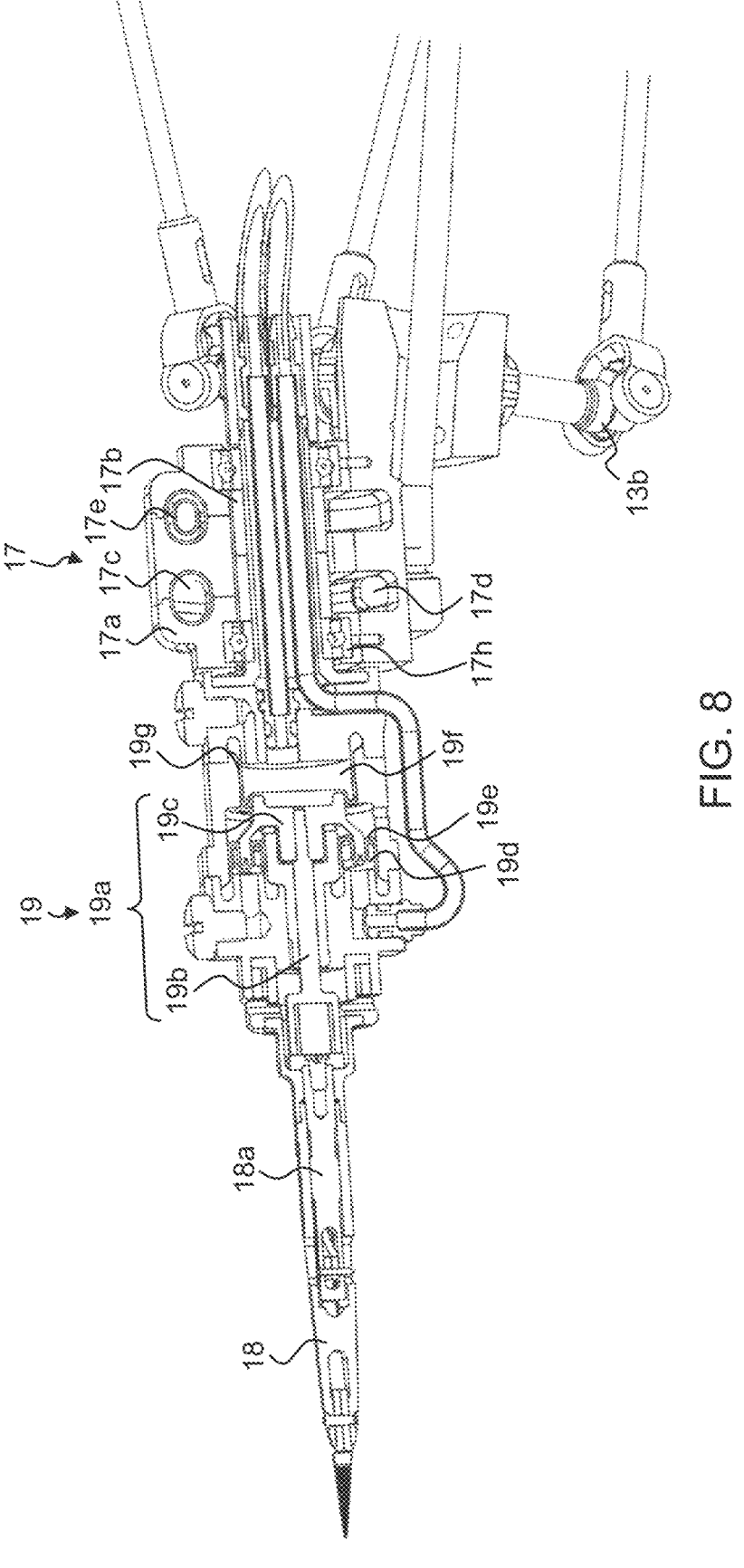
FIG. 8 is a partially cutaway perspective view showing the end effector and the rotation support part of the manipulator for microscopic work according to the embodiment.
Figure 9:
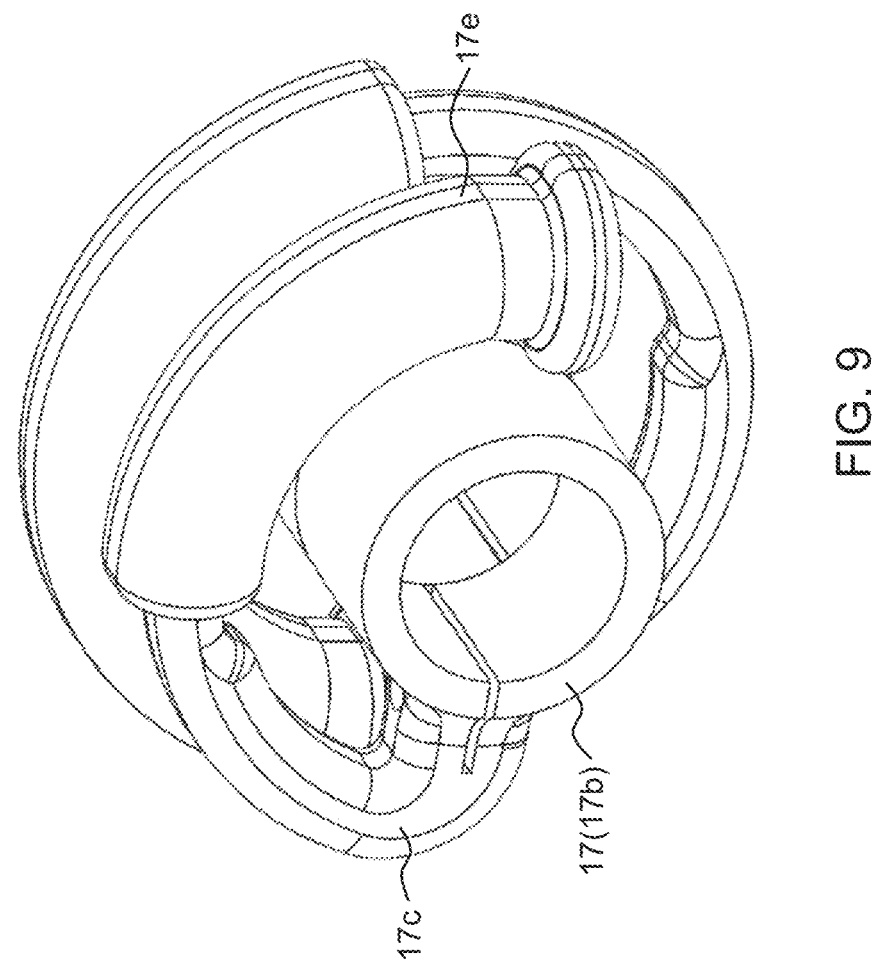
FIG. 9 is a perspective view showing a hydraulic drive mechanism of the manipulator for microscopic work according to the embodiment.

Next, the manipulator for microscopic work 10 of the present embodiment will be described with reference to FIGS. 4 to 6.

The manipulator for microscopic work 10 includes a base that is not shown and is supported by the robot part 20, an end effector 12 that handles the surgery object or a surgical instrument, six links 13 that are disposed in parallel, a rotation support part 17 that is disposed between the base and the end effector 12, and six linear actuators 14 that are supported on the base and shift the individual links 13.

The base, the end effector 12, the links 13, and the linear actuators 14 constitute a parallel link mechanism with six degrees of freedom in which the linear actuators 14 are used to linearly shift one end part of each of the links 13 so as to move the end effector 12 coupled to the other end part of the links 13.

The parallel link mechanism is capable of changing the position and the orientation of the end effector 12 that handles the surgery object or the surgical instrument with respect to the base in a predetermined range and, the parallel link mechanism has six degrees of freedom, and hence the parallel link mechanism can give movement equal to movement in the case where the end effector 12 is supported by a hand to the end effector 12 at the tip.

The linear actuator 14 is a moving-coil linear motor in which a coil 15*b* constitutes a part of a mover 15 and a permanent magnet 16*a* constitutes a part of a stator 16.

The mover 15 includes a linear-motion slider 15*a* that is provided so as to be able to move linearly with respect to the base, a thin cylindrically disposed coil 15*b* that is integrally mounted to the linear-motion slider 15*a* such that its moving direction is parallel to the linear-motion slider 15*a*, and a coupling member 15c that is mounted to a tip of the coil 15b and couples the coil 15b and the linear-motion slider 15a. One end part of the link 13 is coupled and fixed to a tip of the linear-motion slider 15a in the mover 15 via the coupling member 15c, and it follows that the one end part of the link 13 linearly moves together with the mover 15 including the linear-motion slider 15a.

The stator 16 includes a permanent magnet 16a that is formed into a cylindrical shape that is thicker and shorter than the coil 15b of the mover 15, and is fixed to the base by fixing means that is not shown.

In the stator 16, the cylindrical permanent magnet 16a fixed to the base is aligned with the coil 15b of the mover 15 in a cylinder axis direction, and the coil 15b is disposed so as to movably penetrate a cylinder inner space part of the permanent magnet 16b.

Thus, by using the linear motor as the linear actuator 14, as compared with other linear-motion mechanisms such as a ball screw and the like, it is possible to reduce a mechanical movable part and also reduce a contact part involving sliding or rolling, and it is possible to increase reliability as the mechanism and suppress power consumption required for drive by reducing frictional resistance without causing backlash.

The linear actuators 14 that are linear motors constituted by the movers 15 and the stators 16 are parallel to each other in the moving direction of each mover 15, and are arranged to be disposed around a predetermined virtual center line that is parallel to the moving direction of the mover 15 and extends in a longitudinal direction of each linear actuator 14 such that the permanent magnet 16a of each stator 16 and the coil 15b of each mover 15 are closest to the virtual center line, and the individual permanent magnets 16a are disposed at regular intervals and the individual coils 15b are disposed at regular intervals around the virtual center line.

Note that, while the permanent magnet 16a constituting the stator 16 is disposed so as to penetrate the cylinder inner space part to be close to the other coils 15b other than the coils 15b constituting a pair of the linear motors, unlike the coil 15b, the fixed permanent magnet 16a does not have fluctuation of a magnetic field, and hence the permanent magnet 16a does not exert a magnetic influence on the movement of each of the other coils 15b.

The movers 15 and the stators 16 of the individual linear motors constituting the linear actuators 14 are disposed to be arranged around the virtual center line, and hence the linear actuator parts of the manipulator for microscopic work 10 can be integrated into a compact structure. Further, the end part of the coil 15b of the mover 15 that fluctuates a fixed magnetic field does not approach the permanent magnet 16a of the stator 16 significantly due to a mechanical structure, and hence it is possible to suppress the fluctuation of the magnetic field that causes cogging against the movement of the mover 15, and it is possible to implement the smooth operation of the linear actuator 14.

The link 13 is configured such that joints 13a and 13b each having a plurality of degrees of freedom for being coupled to the linear actuator 14 and the rotation support part 17 are provided at both ends of a bar-shaped body in which substantially bar-shaped two members that have high rigidity and don't deform are coupled and combined with each other in a longitudinal direction. This link 13 has a structure in which the substantially bar-shaped members that constitute the bar-shaped body are rotatably coupled to each other and a certain degree of freedom of rotation about an axis parallel to a mutual longitudinal direction is provided between a part of the link 13 close to one end and a part of the link 13 close to the other end.

The joint 13a at one end part of the link 13 has a structure having a certain degree of freedom of each of rotations about two axes that are orthogonal to each other, and is coupled to the end part of the linear-motion slider 15a of the linear actuator 14. In addition, the joint 13b at the other end part of the link 13 has a structure having a certain degree of freedom of each of rotations about two axes that are orthogonal to each other similarly to the above description, and is coupled to the rotation support part 17.

With the provision of a certain degree of freedom of rotation between the part of the link 13 close to one end and the part of the link 13 close to the other end, and the couplings by the joints 13a and 13b each having a certain degree of freedom of each of two rotations at both end parts of the link 13, each link 13 can freely change the orientation with respect to the linear actuator 14 and the rotation support part 17 coupled to the link 13 similarly to the case where coupling is performed by using a ball joint. In addition, by using the link mechanism in which the link 13 is disposed between the linear actuator 14 and the rotation support part 17 in the parallel link mechanism in which six links 13 are disposed in parallel, there is provided a system in which various movements related to changes of the position and the orientation of each of the rotation support part 17 and the end effector 12 provided at the tip part of the rotation support part 17 are permitted with six degrees of freedom in which three degrees of freedom of movement in directions of three axes that are orthogonal to each other and three degrees of freedom of each of the rotations about the three axes are combined similarly to the case where the end effector 12 is supported by a hand of a person.

Next, with reference to FIGS. 7 to 15, a description will be given of the end effector 12 and the rotation support part 17 in the manipulator for microscopic work 10 of the present embodiment.

The rotation support part 17 includes an outer tubular member 17a that is formed into an outer diameter tubular shape, and an inner tubular member 17b that is accommodated in a hollow part of the outer tubular member 17a similarly. Inside the outer tubular member 17a, a doughnut-shaped hollow part 17c is formed around the center axis of the outer tubular member 17a.

As shown in detail in FIGS. 9 to 12, the inner tubular member 17b is provided with an arc-shaped guide member 17d that protrudes from the inner tubular member 17b and extends around the center axis of the inner tubular member 17b (this center axis matches the center axis of the outer tubular member 17a). On an outer periphery of the guide member 17d, a rolling diaphragm 17e made of a stretchable material such as, e.g., silicone rubber is provided.

Figure 15:
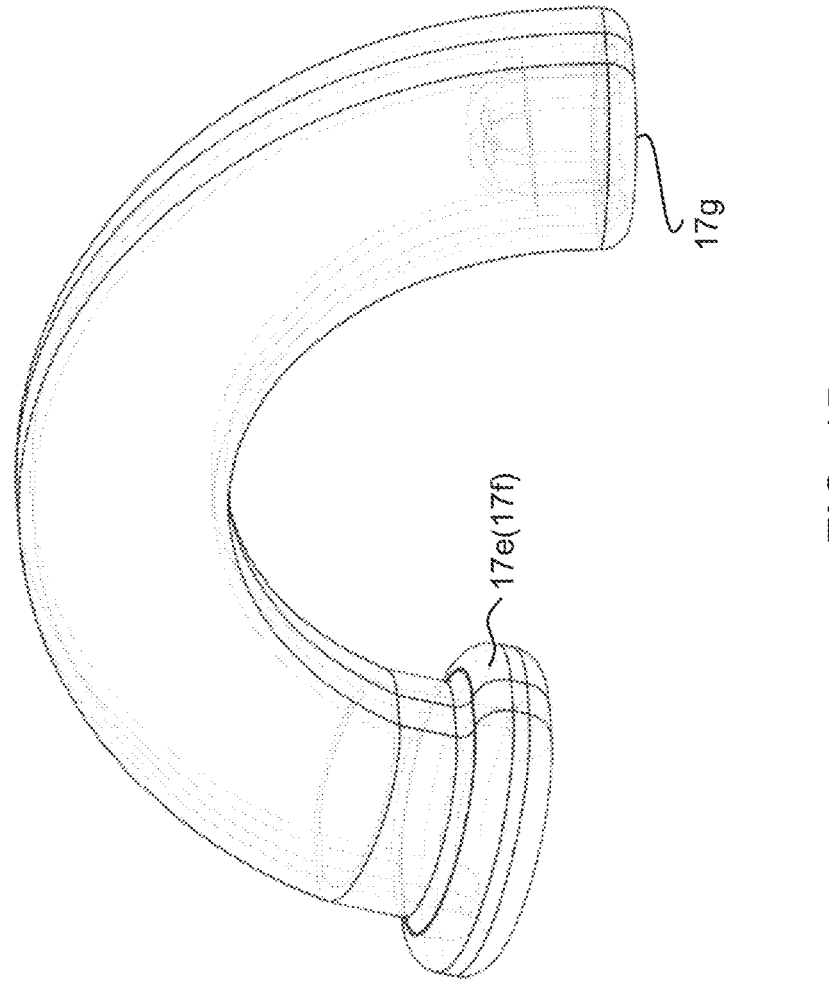
FIG. 15 is a perspective view showing the diaphragm of the manipulator for microscopic work according to the embodiment.

As shown in FIG. 15, the rolling diaphragm 17e includes a diaphragm main body 17f that is formed into an arc shape having substantially the same center as that of the guide member 17d, and an arc-shaped concave part 17g that is formed on the side of one end of the diaphragm main body 17f (on the side of a right end in FIG. 15) and is formed to be slightly larger in diameter than the outer periphery of the guide member 17d. In addition, as shown in FIGS. 9 to 12, the guide member 17d of the inner tubular member 17b is fitted in the concave part 17g of the rolling diaphragm 17e.

In the diaphragm main body 17f, a concave part that is not shown is also formed on a side opposite to the temporary side on which the concave part 17g is provided, and a working fluid is supplied to this concave part from a hydraulic pressure supply mechanism described later. That is, the concave part in the diaphragm main body 17f functions as a working fluid chamber.

Figure 11:
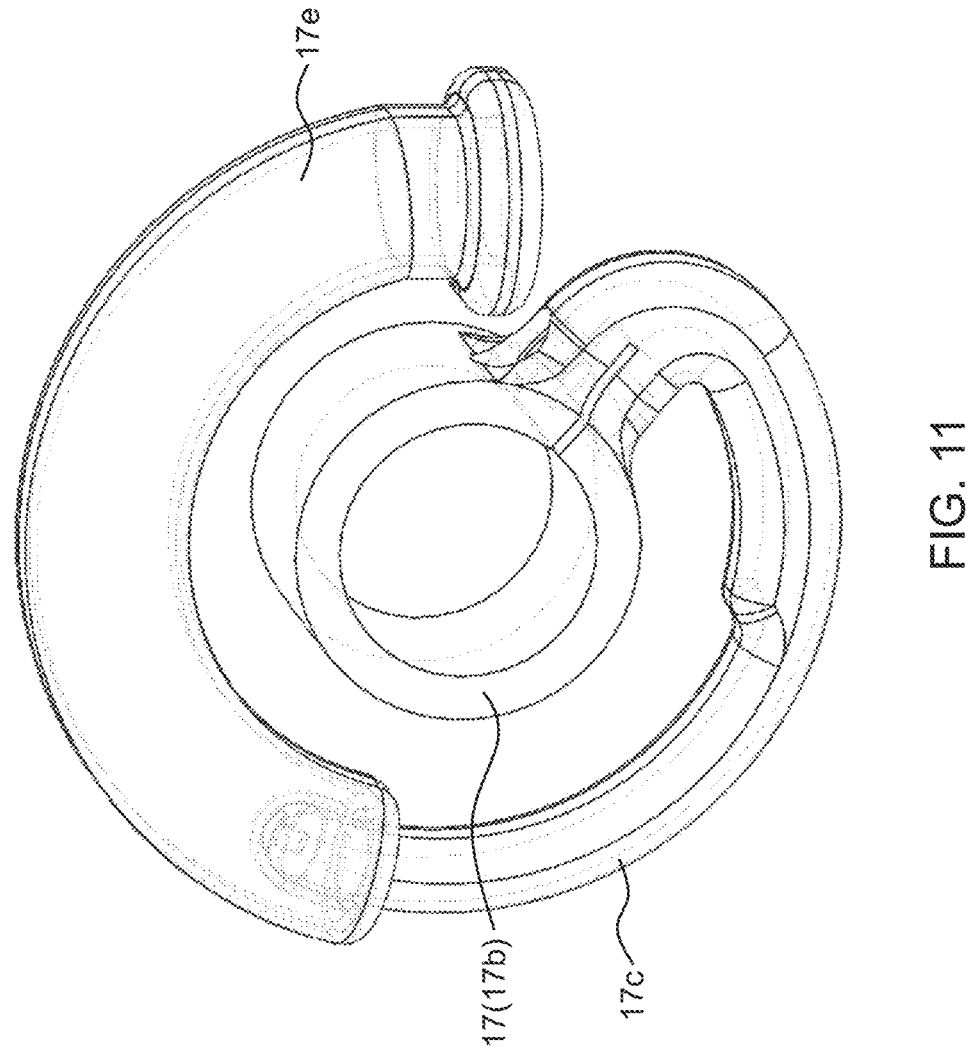
FIG. 11 is a perspective view showing a guide member and a diaphragm of the manipulator for microscopic work according to the embodiment.
Figure 12:
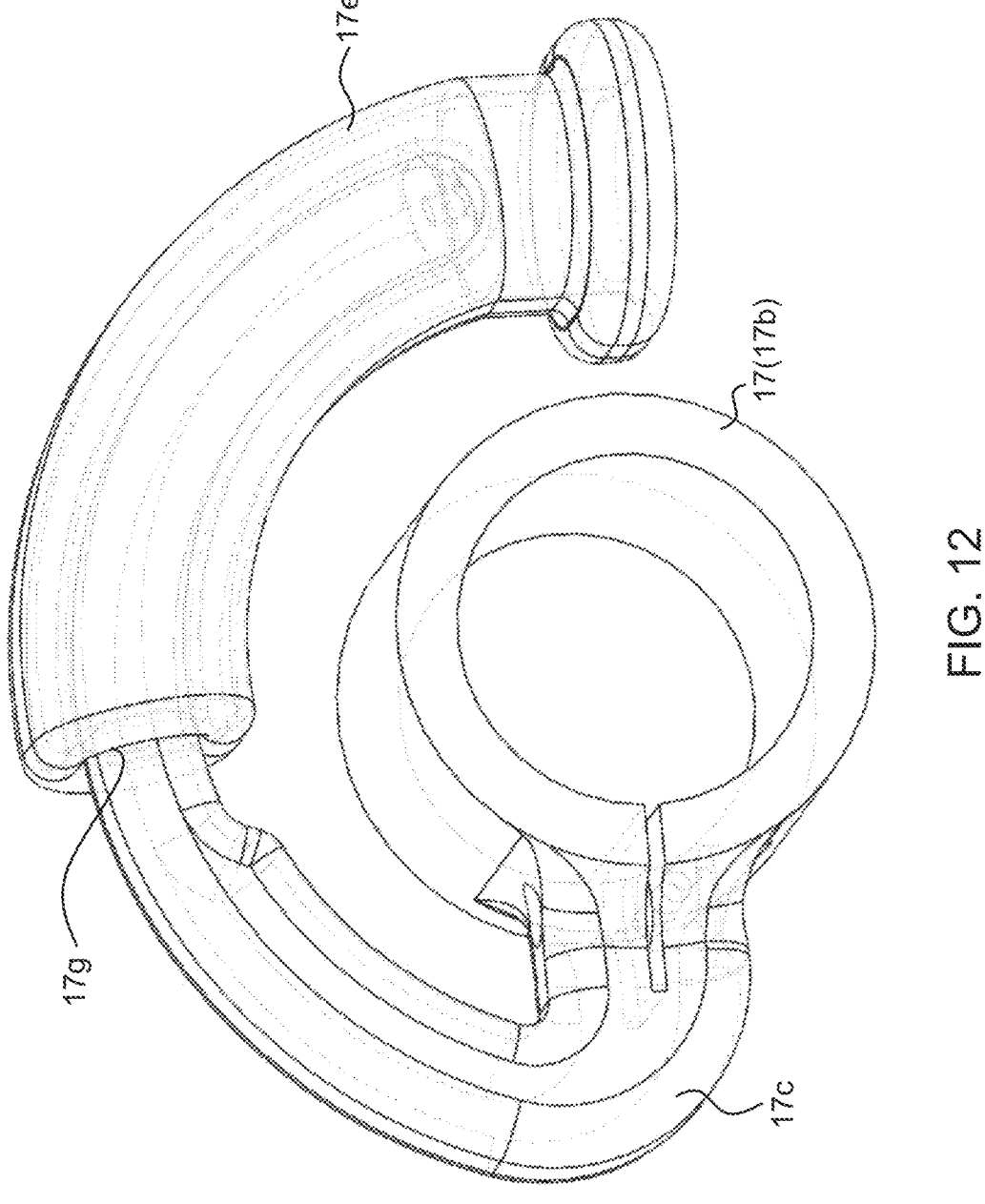
FIG. 12 is a perspective view showing the guide member and the diaphragm of the manipulator for microscopic work according to the embodiment.
Figure 13:
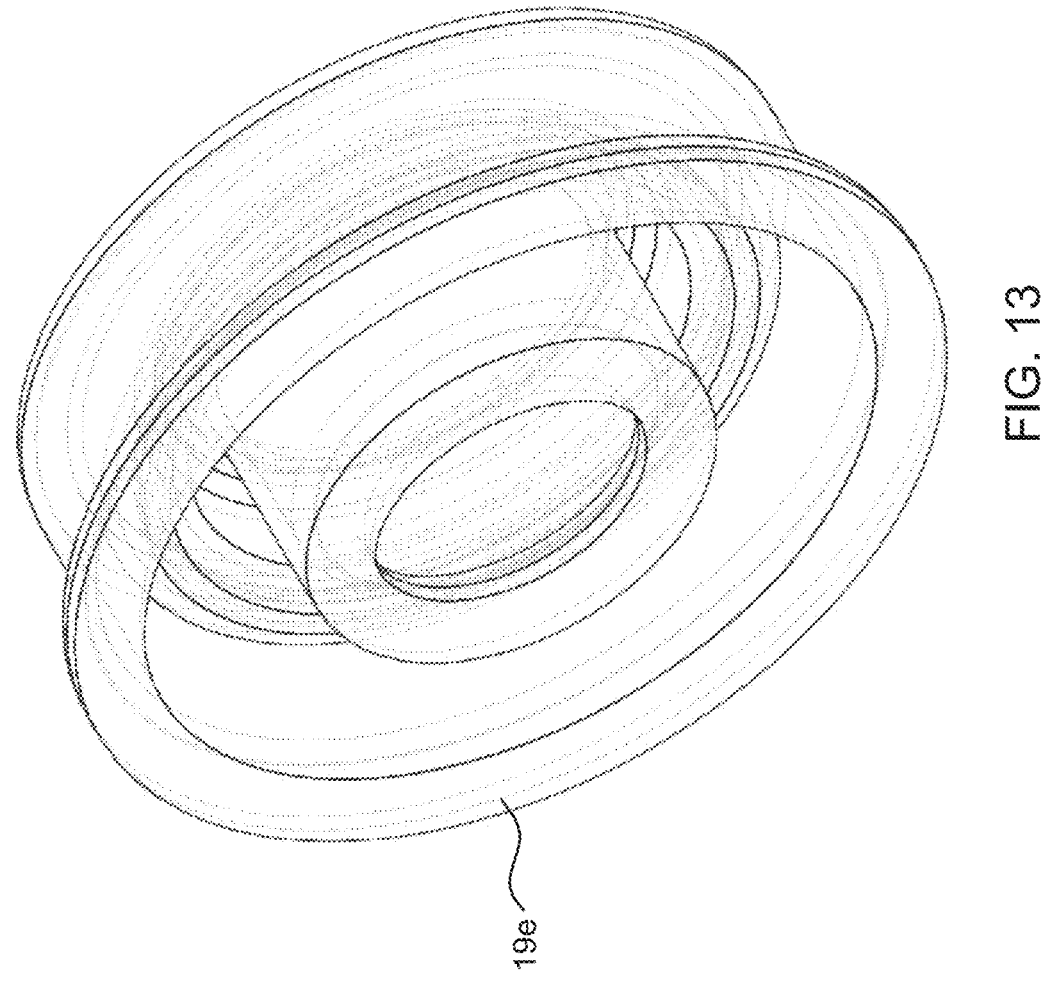
FIG. 13 is a perspective view showing the diaphragm provided in the end effector of the manipulator for microscopic work according to the embodiment.

With this, the volume of the concave part 17g of the rolling diaphragm 17e is increased or decreased by the working fluid and, with this, the guide member 17d rotates along the center axis of the inner tubular member 17b. FIG. 11 shows a state in which the inside of the diaphragm main body 17f of the rolling diaphragm 17e is filled with the working fluid and, as a result, the guide member 17d is rotated counterclockwise in the drawing. On the other hand, FIG. 12 shows a state in which the working fluid is discharged from the inside of the diaphragm main body 17f of the rolling diaphragm 17e and, as a result, the guide member 17d is rotated counterclockwise in the drawing.

Figure 10:
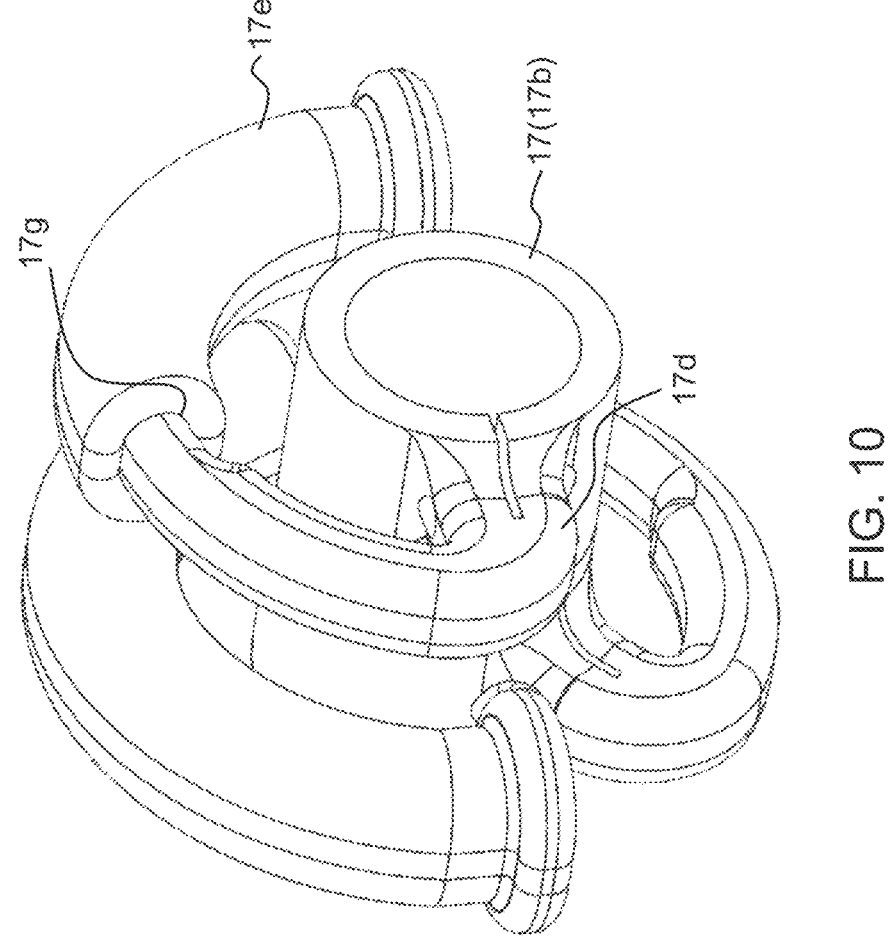
FIG. 10 is a perspective view showing the hydraulic drive mechanism of the manipulator for microscopic work according to the embodiment.

As shown in FIG. 10, the outer tubular member 17a and the inner tubular member 17b are fixed so as to be rotatable relative to each other by a bearing 17h. In addition, the outer tubular member 17a is fixed to the joint 13b of the link 13. Consequently, the inner tubular member 17b is rotated relative to the outer tubular member 17a in response to an increase or a decrease in hydraulic pressure by working fluid supply. This inner tubular member 17b is coupled to the end effector 12, and hence, as a result, the end effector 12 is also rotated in response to an increase or a decrease in hydraulic pressure by the working fluid supply.

Consequently, the inner tubular member 17b and the rolling diaphragm 17e of the rotation support part 17 correspond to a hydraulic drive mechanism that generates rotating power around the center axis of the inner tubular member 17b in the end effector 12.

The end effector 12 can execute handling of the surgery object or the surgical instrument. Specifically, this end effector 12 includes a tip operation part 18 that executes the handling of the surgery object or the surgical instrument with movement of opening and closing with one degree of freedom that is separate from overall movement by the parallel link mechanism, and a hydraulic drive mechanism 19 that generates the movement of handling the surgery object or the surgical instrument of this tip operation part 18.

Among them, the tip operation part 18 is detachably attached to the hydraulic drive mechanism 19, and can be separated from the hydraulic drive mechanism 19 and can be replaced.

Thus, there is provided a system in which, in the end effector 12, only the tip operation part 18 that actually executes the handling of the surgery object or the surgical instrument can be easily replaced with a tip operation part suitable for the surgery object or a situation, and work related to the surgery can be thereby performed efficiently.

Specifically, the tip operation part 18 is formed into a substantially conical shape having two end parts constituting forceps parts that can open and close to hold the surgery object or the surgical instrument between them, and is detachably attached to the hydraulic drive mechanism 19. This tip operation part 18 includes a rod part 18a that can move linearly in synchronization with the forceps parts that open and close, and the forceps parts are allowed to open and close by moving the rod part 18a with the hydraulic drive mechanism 19.

Examples of the replaceable tip operation part 18 of the end effector 12 include, in addition to the forceps, scissors, tweezers, a needle holder, a bipolar (high-frequency energizing coagulation instrument), and disposable forceps. In addition, the tip operation part can be replaced with a tip operation part that needs only the movement of the entire end effector by the linear actuator and does not require an independent operation by the hydraulic drive mechanism when work related to the surgery is executed such as, e.g., an electric knife (so-called monopolar), and the electric knife can be used.

The hydraulic drive mechanism 19 includes a hydraulic cylinder part 19a that causes a rod 19b and a piston 19c that are supported so as to be able to move linearly to reciprocate in response to change in working-fluid hydraulic pressure. There is provided a system in which, when the tip operation part 18 is attached to this hydraulic drive mechanism 19, the rod 19b of the hydraulic drive mechanism 19 is coupled to the rod part 18a of the tip operation part 18, and movement corresponding to the change in hydraulic pressure of the hydraulic cylinder part 19a is transferred to the forceps parts of the tip operation part 18 in synchronization.

The hydraulic cylinder part 19a changes the volume of a working fluid chamber 19d inside the cylinder with the change in the hydraulic pressure of the working-fluid imparted from the exterior to move the piston 19c, and transfers the movement of the piston 19c to the rod part 18a of the tip operation part 18 via the rod 19b to generate an opening-closing operation of the forceps parts. Between the piston 19c and the working fluid chamber 19d of the hydraulic cylinder part 19a, there is provided a rolling diaphragm 19e that partitions the inside of the cylinder into an area in which the piston 19c is present and the working fluid chamber 19d while deforming correspondingly to the movement of the piston 19c, and maintains a fluid-tight state between the piston 19c and the working fluid chamber 19d (see FIG. 13).

Figure 14:
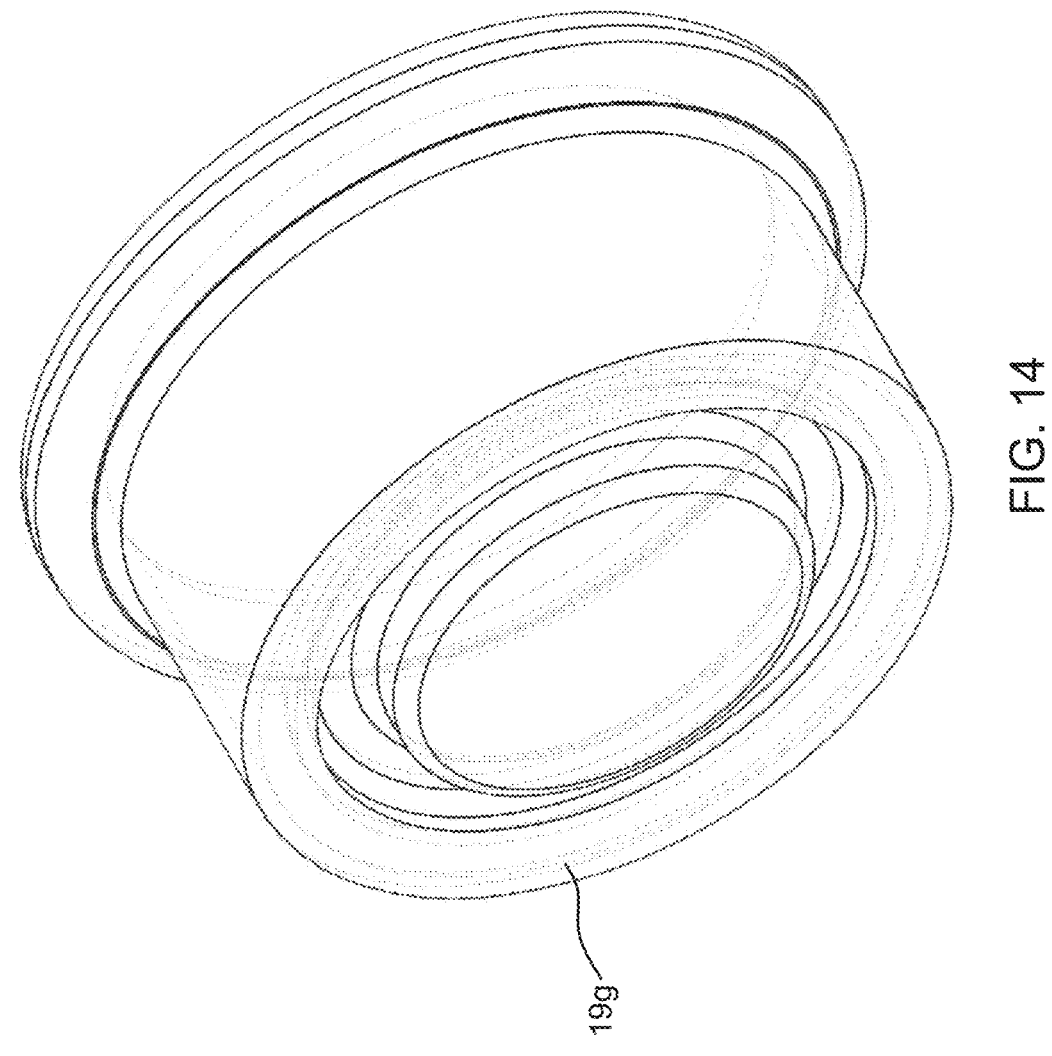
FIG. 14 is a perspective view showing the diaphragm provided in the end effector of the manipulator for microscopic work according to the embodiment.

Similarly, a working fluid chamber 19f is formed also in a rear end part (a right end part in FIG. 10) of the piston 19c of the hydraulic cylinder part 19a and, between the piston 19c and the working fluid chamber 19f of the hydraulic cylinder part 19a, there is provided a rolling diaphragm 19g that maintains the fluid-tight state between the piston 19c and the working fluid chamber 19f while deforming correspondingly to the movement of the piston 19c (see FIG. 14). In addition, the hydraulic cylinder part 19a changes the volume of the working fluid chamber 19f inside the cylinder with the change in the hydraulic pressure of the working-fluid imparted from the exterior to move the piston 19c, and transfers the movement of the piston 19c to the rod part 18a of the tip operation part 18 via the rod 19b to generate the opening-closing operation of the forceps parts.

Herein, similarly to the rolling diaphragm 17e, the rolling diaphragms 19e and 19g are formed of a stretchable material such as, e.g., silicone rubber.

To the working fluid chambers 19d and 19f of the hydraulic drive mechanism 19 of the end effector 12, the working fluid is supplied from a hydraulic pressure supply mechanism described later.

In addition, there may be provided a sheet-shaped antibacterial cover that covers an entire slave part other than the tip operation part 18 that can be separated from the other part of the end effector 12 and can be replaced, and the tip operation part 18 of the end effector may be configured to be attachable to and detachable from the hydraulic drive mechanism 19 by using, e.g., a magnet or the like even in a state in which the cover is provided.

In the case where the above-described cover is provided, it is possible to secure cleanliness of an area in which the surgery object is present by reliably separating, as a space, an area in which the slave part other than the tip operation part 18 is present, i.e., an area in which sterilization work cannot be performed due to the presence of various movable mechanisms and energized parts and it is difficult to secure cleanliness from an area in which the tip operation part 18 that can be sterilized and can ensure cleanliness, and the surgery object are present by using the cover.

Note that the end effector 12 is configured such that the tip operation part 18 is attachable to and detachable from the hydraulic drive mechanism 19 and, besides this, the end effector 12 can also be configured such that the tip operation part 18 and the hydraulic drive mechanism 19 are integrally handled and are configured to be attachable to and detachable from the rotation support part 17, and a tip side part including the tip operation part 18 and the hydraulic drive mechanism 19 can be separated from the rotation support part 17 coupled to the other end parts of six links 13 constituting the parallel link mechanism and can be replaced and, similarly, by replacing the tip operation part 18 together with the hydraulic drive mechanism 19 with a tip operation part suitable for the surgery object or the situation, work related to the surgery can be performed efficiently.

In addition, the configuration is not limited to the configuration in which the tip operation part 18 is configured to be attachable and detachable, and a configuration may also be adopted in which the end effector 12 is formed as an integral structure extending from the rotation support part 17 to the tip operation part 18 that cannot be separated.

Figure 16:
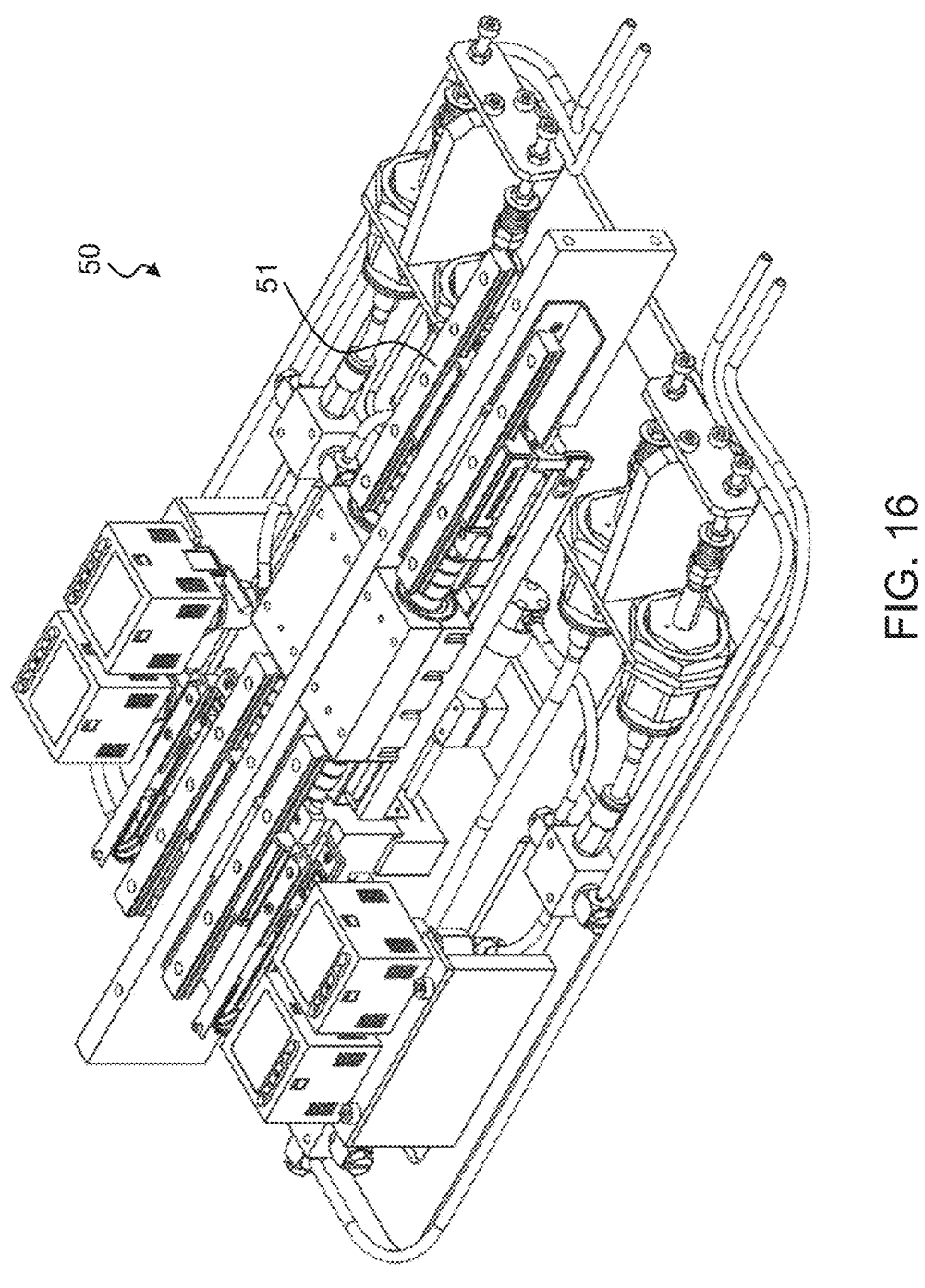
FIG. 16 is a perspective view showing a hydraulic pressure supply mechanism of the manipulator for microscopic work according to the embodiment.
Figure 17:
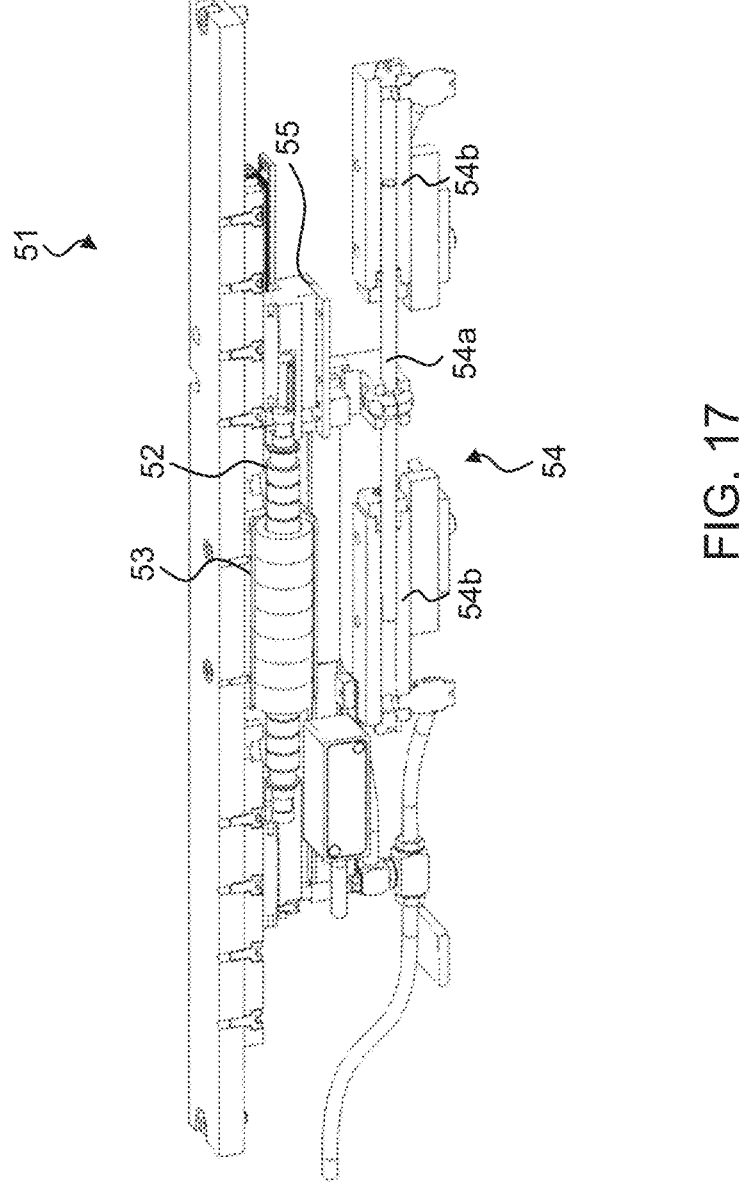
FIG. 17 is a partially cutaway perspective view showing the hydraulic pressure supply mechanism of the manipulator for microscopic work according to the embodiment.

Next, with reference to FIGS. 16 and 17, a description will be given of the hydraulic pressure supply mechanism in the device for microscopic work 1 of the present embodiment.

A hydraulic pressure supply mechanism 50 that supplies the working fluid to the manipulator for microscopic work 10 of the device for microscopic work 1 to change the hydraulic pressure of the working fluid includes a linear actuator 51 constituted by a mover 52 and a stator 53 having the same structures as those of the mover 15 and the stator 16 of the manipulator for microscopic work 10, and a hydraulic cylinder part 54 that is operated by this linear actuator 51.

The hydraulic cylinder part 54 includes a columnar piston 54a and a pair of cylindrical cylinders 54b provided at both ends of the piston 54a. The cylinder 54b is filled with the working fluid that is not shown. In addition, the mover 52 of the linear actuator 51 and the piston 54a are coupled to each other by a fixing member 55, whereby the piston 54a slides in the cylinder 54b in response to the movement of the mover 52 of the linear actuator 51 and, as a result, differential hydraulic pressure is applied to the working fluid in the cylinder 54b. This working fluid is supplied to the manipulator for microscopic work 10.

Next, a description will be given of the operation of the device for microscopic work 1 of the present embodiment. First, an operator of the device for microscopic work 1 moves the robot part 20 including the manipulator for microscopic work 10 to the vicinity of the patient 2 who lies on the surgical table 3 by moving the base 30 via the control part that is not shown, and further positions the tip operation part 18 of the manipulator for microscopic work 10 in the vicinity of an affected part of the patient 2 serving as the surgery object by moving the individual parts of the robot part 20 via the control part that is not shown. In addition, the operator of the device for microscopic work 1 moves each part of the imaging part 40 such that an image of an area including the vicinity of the affected part of the patient 2 can be captured by the imaging part 40 via the control part.

In this state, in the case where it is necessary to perform the operation of rotating (twisting) the end effector 12 to a desired orientation with respect to the surgery object, or hold a predetermined part of the surgery object or grasp the surgical instrument such as a needle for inosculation or suture with the tip operation part 18, the operator of the device for microscopic work 1 operates the hydraulic pressure supply mechanism 50 via the control part to adjust the hydraulic pressure of the working fluid.

The guide member 17d of the rotation support part 17 is rotated about the center axis of the inner tubular member 17b by the hydraulic pressure adjustment by the working fluid supply of the hydraulic pressure supply mechanism 50, whereby the end effector 12 including the tip operation part 18 provided at the tip part of the rotation support part 17 is rotated, and the twisting operation of the end effector 12 is thereby implemented.

Note that, in the manipulator for microscopic work 10 of the present embodiment, the rotation support part 17 and the end effector 12 including the tip operation part 18 can be rotated also by the linear actuator 14 and the link 13. However, when the end effector 12 is rotated (twisted) by an angle required by surgery work or the like (e.g., ±90°) by operations of only the linear actuator 14 and the link 13, there is a possibility that the link 13 may vibrate and the tip operation part 18, particularly the forceps parts may vibrate. On the other hand, it is difficult to rotate the rotation support part 17 by ±90° due to its structure, and the rotation of the rotation support part 17 is limited to a rotation range of about ±70°.

To cope with this, in the manipulator for microscopic work 10 of the present embodiment, the twisting (rotational) operation of the end effector 12 is performed mainly by the rotation support part 17, and the twisting operation by the linear actuator 14 and the link 13 is performed in a range in which the smooth operation is expected to be performed by the linear actuator 14 and the link 13 (about ±20° in the above-described example). With this, it is possible to implement the stable twisting operation of the forceps parts while securing the rotation angle required by the end effector 12.

In addition, the rod 19b of the end effector 12 is moved by the hydraulic pressure adjustment by the working fluid supply of the hydraulic pressure supply mechanism 50, and the rod part 18a of the tip operation part 18 is thereby moved, and the forceps parts are thereby caused to open and close.

The twisting operation of the end effector 12 and the opening-closing operation of the forceps parts of the tip operation part 18 are performed separately from the movement of each part of the robot part 20 and the movement of the position and the orientation of the manipulator for microscopic work 10 (i.e., the movement of the position and the orientation of the end effector 12).

With this, separately from the operation of changing the position and the orientation of the end effector 12, the operation in which the forceps parts of the tip operation part 18 move to hold the predetermined part of the surgery object or grasp the surgical instrument is executed.

The operator of the device for microscopic work 1 can operate the device for microscopic work 1 including the manipulator for microscopic work 10 according to the above procedure, can move the tip operation part 18 of the end effector 12 to hold or release a blood vessel or the like serving as the surgery object and grasp or release the surgical instrument such as a needle, and can properly operate the end effector 12 and the tip operation part 18 to cause the end effector 12 and the tip operation part 18 to execute accurate work such as, e.g., passing a needle for inosculation grasped by the tip operation part 18 through a vessel joint part in addition to the operation of moving the entire manipulator for microscopic work 10 while viewing the display part.

As has been described in detail thus far, in the device for microscopic work 1 according to the present embodiment, the parallel link mechanism with a plurality of degrees of freedom is used as the link mechanism in which the end effector 12 is movable with respect to the base, a plurality of the linear actuators 14 that are supported on the base are used to shift one end part of each of the links so as to move the end effector 12, the linear actuator 14 is operated based on an instruction from the operator, and the position and the orientation of the end effector 12 are thereby changed, and hence it is possible to implement the accurate movement of the end effector 12 with the simple link mechanism having high rigidity in which errors are unlikely to be accumulated, it is possible to cause the end effector 12 to perform various operations related to microsurgery even with remote operations of a user who is viewing a displayed captured image, and it is possible to improve workability and reduce a burden on the user while allowing the reproduction of operations equal to manipulation of a skilled surgeon.

In addition, the rotation operation of the end effector 12 and the tip operation part 18 that executes the actual handling of the surgery object or the surgical instrument are configured to be hydraulically driven, whereby it is not necessary to provide a sensor for power detection used in the case of motor drive in the tip operation part 18, troublesome work such as calibration of a sensor becomes unnecessary, a reduction in the size of the end effector 12 is allowed, and sterilization work for the end effector 12 when the end effector 12 is used in surgery is facilitated.

In addition, the working fluid is supplied into the working fluid chambers 19d and 19f defined by the rolling diaphragms 17e, 19e, and 19g, and hence it is not necessary to provide packing when the rotation support part 17 and the hydraulic drive mechanism 19 are moved and, accordingly, a frictional force does not act when the rotation support part 17 and the hydraulic drive mechanism 19 are moved due to absence of a sliding surface. Further, each of the rolling diaphragms 17e, 19e, and 19g is formed of a stretchable material such as, e.g., silicone rubber, and there is provided an advantage that responsiveness of each of the end effector 12 and the tip operation part 18 to minute hydraulic pressure fluctuation of the working fluid supply is excellent. In addition, each of the rolling diaphragms 17e, 19e, and 19g is fixed to the rotation support part 17 and the hydraulic drive mechanism 19, and hence there is provided an advantage that the rolling diaphragms 17e, 19e, and 19g are resistant to leakage of the working fluid.

Note that, in the above-described embodiment, the configurations have been described in detail for easy-to-understand description of the present invention, and the present invention is not necessarily limited to the embodiment including all of the above-described configurations. In addition, some of the configurations in the embodiment may be added to, deleted from, or replaced with other configurations.

As an example, in the above-described embodiment, while the manipulator for microscopic work 10 is mounted to the robot part 20 and the base 30, a configuration may also be adopted in which, with regard to coarse adjustment of the position or the like of the manipulator for microscopic work 10 with respect to the surgery object, the adjustment is performed by manually moving a stand and an arm such that the end effector 12 is directed to the surgery object and also has a proper distance to the surgery object in a state in which the manipulator for microscopic work 10 is temporarily mounted to and supported by the stand and the arm for supporting the manipulator for microscopic work 10.

In the above-described embodiment, the control lines and the information lines considered necessary for the description have been described, and all of the control lines and the information lines necessary for a product are not necessarily described. All of the configurations may be connected to each other.

REFERENCE SIGNS LIST

1 Device for microscopic work
10 Manipulator for microscopic work
12 End effector
13 Link
14 Linear actuator
15 Mover
15a Linear-motion slider
15b Coil
16 Stator
16a Permanent magnet
17 Rotation support part
17a Outer tubular member
17b Inner tubular member
17c Hollow part
17d Guide member
17e Rolling diaphragm
17f Diaphragm main body
17g Concave part
18 Tip operation part
19 Hydraulic drive mechanism

The invention claimed is:

1. A manipulator for microscopic work that executes a predetermined operation related to microscopic work on a work object instead of a person, the manipulator for microscopic work comprising:
a tip operation part that is configured to execute a handling operation of the work object or an instrument for work;
a link mechanism that is configured to be capable of changing a position and an orientation of the tip operation part in a space in which the work object is present; and
a support part that is between the link mechanism and the tip operation part and is configured to support the tip operation part on the link mechanism, wherein
the support part includes a first drive mechanism that is configured to drive the tip operation part to generate the handling operation and a second drive mechanism that is configured to rotate the tip operation part around a predetermined rotational axis, and not only the second drive mechanism but also the link mechanism is configured to be capable of rotating the tip operation part around predetermined rotational axis, wherein
the rotation of the tip operation part is performed in a first angle range by using the link mechanism,
the rotation of the tip operation part by using the second drive mechanism is performed in a second angle range,
a size of the first angle range is different from a size of the second angle range, and
the first angle range is smaller than the second angle range.

2. A manipulator for microscopic work that executes a predetermined operation related to microscopic work on a work object instead of a person, the manipulator for microscopic work comprising:
a tip operation part that is configured to execute a handling operation of the work object or an instrument for work;

a link mechanism that is configured to be capable of changing a position and an orientation of the tip operation part in a space in which the work object is present; and a support part that is between the link mechanism and the tip operation part and is configured to support the tip operation part on the link mechanism, wherein the support part includes a first drive mechanism that is configured to drive the tip operation part to generate the handling operation and a second drive mechanism that is configured to rotate the tip operation part around a predetermined rotational axis, and not only the second drive mechanism but also the link mechanism is configured to be capable of rotating the tip operation part around predetermined rotational axis, wherein the rotation of the tip operation part is performed in a first angle range by using the link mechanism, the rotation of the tip operation part by using the second drive mechanism is performed in a second angle range, a size of the first angle range is different from a size of the second angle range, and an angle range obtained by adding the first angle range and the second angle range is equal to a predetermined required angle range that is required for the microscopic work.

3. The manipulator for microscopic work according to claim 2, wherein the required angle range is from −90 degrees to +90 degrees.

4. A manipulator for microscopic work that executes a predetermined operation related to microscopic work on a work object instead of a person, the manipulator for microscopic work comprising:

a tip operation part that is configured to execute a handling operation of the work object or an instrument for work;

a link mechanism that is configured to be capable of changing a position and an orientation of the tip operation part in a space in which the work object is present; and a support part that is between the link mechanism and the tip operation part and is configured to support the tip operation part on the link mechanism, wherein the support part includes a first drive mechanism that is configured to drive the tip operation part to generate the handling operation and a second drive mechanism that is configured to rotate the tip operation part around a predetermined rotational axis, and not only the second drive mechanism but also the link mechanism is configured to be capable of rotating the tip operation part around predetermined rotational axis, wherein the second drive mechanism includes a guide member that is arc shaped about the rotational axis and is supported to be rotatable around the rotational axis and to which rotating power around the rotational axis is imparted.

\*    \*    \*    \*    \*